United States Patent [19]

Dahod

[11] Patent Number: 4,613,690

[45] Date of Patent: Sep. 23, 1986

[54] RACEMIZATION OF OPTICALLY ACTIVE COMPOUNDS HAVING A BROMINE SUBSTITUTED CHIRAL CARBON ATOM

[75] Inventor: Samun K. Dahod, Yorktown Heights, N.Y.

[73] Assignee: Stauffer Chemical Company, Westport, Conn.

[21] Appl. No.: 771,092

[22] Filed: Aug. 30, 1985

[51] Int. Cl.$^4$ ............................................ C07B 55/00
[52] U.S. Cl. .................................. 562/401; 562/402; 562/490; 562/492; 562/493; 562/602
[58] Field of Search ................................ 562/401, 402

[56] References Cited

U.S. PATENT DOCUMENTS 4,237,313 12/1980 Higo et al. .......................... 562/401

*Primary Examiner*—Natalie Trousof
*Assistant Examiner*—Vera C. Clarke
*Attorney, Agent, or Firm*—Paul J. Juettner

[57] ABSTRACT

Optically active compounds having a chlorine atom attached to the chiral carbon atom such as 2-bromoaliphatic acids can be racemized without by-product formation by heating an acidified solution of the organic acid at a temperature sufficient to accomplish racemization, the solution being substantially devoid of ionized halogen other than bromine ions. The preferred acidifying agent is hydrobromic acid. The use of hydrochloric acid causes extensive by-product formation.

17 Claims, No Drawings

RACEMIZATION OF OPTICALLY ACTIVE COMPOUNDS HAVING A BROMINE SUBSTITUTED CHIRAL CARBON ATOM

FIELD OF THE INVENTION

The present invention relates to a process for racemizing optically active compounds having a bromine atom attached to the chiral carbon atom such as 2-bromoaliphatic acids.

BACKGROUND OF THE INVENTION

Certain herbicides such as napropamide, chemical name: 2-(alpha-naphthoxy)-N,N-diethylpropionamide, are active only in the dextro (+) isomeric form. (Synthesis and Herbicidal Activity of N,N-Diethyl-2-(1-naphthyloxy)propionamide & Its Optical Isomers - Agricultural & Food Chemistry, Vol. 23, 5 (Sept/Oct 1975) pp. 1008–1010). It is known that the dextro isomer of napropamide can be prepared from L-methyl-2-bromopropionate. This material is not presently available at a price which can be economically utilized in the process of preparing napropamide as suggested above. Enzymes have shown stereospecificity in resolving mixtures of D,L-methyl-2-bromopropionate into L-methyl-2-bromopropionate and D-2-bromopropionic acid. In order for such a resolution method to provide an economical process it is necessary to racemize and reesterify the D-2-bromopropionic acid for resolution and use in manufacturing the desired product.

THE INVENTION

Optically active compounds having a bromine atom attached to the chiral carbon atom(s), such as bromoaliphatic acids, can be racemized without substantial by-product formation by heating an acidified solution of the optically active compound in the substantial absence of halide ions other than bromine ion in an amount sufficient and at a pH and at a temperature sufficient to accomplish racemization. It has been surprisingly found that the presence of halogen ions other than bromine, such as chloride ions, produces by-product compounds in amounts proportional to the content of such halide ions.

Racemization can be accomplished by refluxing the optically active compound at native pH if the pH is sufficiently low to effect racemization. However, by-products other than chloro-substituted optically active compounds may be formed. It has been found that a reduction in pH to a range from about 1 to about 2.5 in the absence of bromine ions and below 2.5 in the presence of bromine ions along with heating to a sufficient temperature is required for racemization of optically active 2-bromoaliphatic acids to achieve a reduction in by-product formation. Preferably, the racemization is accomplished with hydrobromic acid. The racemization with hydrobromic acid proceeds easily and cleanly without producing yield reducing by-products.

DETAILED DESCRIPTION OF THE INVENTION

The compounds that can be racemized in accordance with the present invention are those optically active compounds having a bromine atom attached to a chiral carbon atom. The chiral carbon atom is not contained in an aromatic or homogeneous or heterogeneous alicyclic ring. The chiral carbon atom is so located within the optically active compound that the groups attached to the chiral carbon do not prevent racemization. The preferred compounds are carboxylic acids which can have an aromatic, e.g. phenylene, or an aliphatic group, e.g. alkylidene, connecting the carboxylic acid group with the chiral carbon atom. Preferably, the compounds are carboxylic acids wherein the chiral carbon atom is attached to the carboxylic acid group. The chiral carbon atom has attached to it other carbon atoms or a hydrogen atom in addition to the bromine atom wherein each is different. A particularly preferred group of compounds which can be racemized in accordance with the invention are the optically active bromoaliphatic acids which can be represented by the formula:

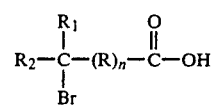

wherein R can be aliphatic or aromatic, n can be an integer of 1 or zero, $R_1$ and $R_2$ each can be hydrogen or alkyl of up to 20 carbon atoms wherein $R_1$ and $R_2$ are different. R can be an organic ring (1 or 2), e.g. phenylene, or aliphatic, e.g. alkyl of up to 20 carbon atoms, as long as the groups do not prevent racemization. Preferably, n is zero, $R_1$ is $C_1$–$C_4$ and more preferably $C_1$–$C_2$ and most preferably $C_1$. $R_2$ is preferably hydrogen. Illustrative of the 2-bromoaliphatic acids which can be racemized in accordance with the invention are D-2-bromopropionic acid, L-2-bromopropionic acid, D-2-bromobutyric acid, D-2-bromopentanoic acid and the like and mixtures thereof.

The following discussion will continue in connection with the preferred optically active bromoaliphatic acids, illustrated by D-2-bromopropionic acid, though the discussion is intended to cover the other optically active compounds falling within the scope of the invention.

The racemization of the optically active bromoaliphatic acids as well as the rate of racemization is pH dependent. The racemization proceeds upon heat treatment at pH's sufficiently low to effect racemization, e.g. racemization proceeds at pH's below about 4 though slowly. Preferably, the pH is below 2.5 for effective reactive rates. It has been found that pH's below about 1 in the absence of bromine ion tend to form by-products other than 2-chloroaliphatic acids which reduce yield. Preferably, a pH within the range of from about 1 to about 2.5 in the absence of bromine ion or below 2.5 in the presence of bromine ion is used for effective racemization without formation of these by-products. Organic acids such as trichloroacetic acid (the trichloroacetic acid would not introduce chlorine ions into the solution) and inorganic mineral acids such as sulfuric acid and hydrobromic acid, the latter being preferred, can be used to acidify the solution. Mineral acids are preferred as they are strong acids and more economical than organic acids which are very weak acids. Other sources of bromide ion include soluble metal bromides which can provide bromide ions under the conditions of racemization. For example, bromides of metals of Groups I and II of the Periodic Table of Elements illustrated by sodium bromide, potassium bromide, lithium bromide and calcium bromide and the like can be used. Any compound which can provide bromine ions under the conditions of the reaction can be used if the compound does not compete with or effect the racemization.

The racemization of the optically active bromoaliphatic acid is generally conducted in the presence of a sufficient amount of water to effect ionization of those acids used for and to the extent needed for racemization. Preferably, an aqueous solution having from about 1% to about 50% bromoaliphatic acid is used. This solution can be made up from the purified bromoaliphatic acid or, preferably, the solution results from the resolution of a racemic mixture of the acid esters. In the preferred embodiment, an aqueous solution of the 2-bromoaliphatic acid results from the resolution of a racemic mixture of the ester with a stereospecific enzyme. For example, the lipase enzyme from the yeast *Candida cylindracea* has been known to hydrolyze the D-isomer ester of 2-bromopropionic acid to thereby resolve the so formed D-isomer acid from the L-isomer ester. These solutions generally have a pH above the pH needed for practical racemization.

The chloro-substituted by-product formation is proportional to the amount of chloride ions present. When 2-bromopropionic acid is racemized in the presence of chloride ion such as from hydrochloric acid, the product will be racemized to 2-chloropropionic acid.

The bromoaliphatic acid can be easily racemized by treatment thereof with hydrobromic acid in an amount sufficient and at a temperature sufficient to effect racemization. The concentration of hydrobromic acid in the aqueous solution is that amount which is sufficient to effect racemization when heated. The hydrobromic acid is used in an amount sufficient to reduce the pH of the bromoaliphatic acid solution to a pH below about 4 and preferably below about 2.5. Hydrobromic acid in normalities of from about 1 to about 12N can be added to an aqueous solution of the bromoaliphatic acid to provide the desired concentration of bromine ions and pH reduction.

The temperature utilized in the racemization reaction is that amount which is sufficient to racemize the bromoaliphatic acid, preferably to an enantiomeric excess of less than about 50% and more preferably less than about 30%. To the extent that small amounts of chlorine ion (less than about 5%) are present, the calculation of the percentage of enantiomeric excess is intended to include any 2-chloro by-product formation. "Enantiomeric excess" is defined as the difference between the predominant optical isomer and subdominant optical isomer. At a ratio of 75:25, the enantiomeric excess is 50%; at 65:35 the excess is 30% and at a ratio of 50:50, the excess is zero. The temperature of treatment preferably ranges from about 50° C. up to and including the reflux temperature of the aqueous bromoaliphatic acid medium. More preferably, reflux temperature is used for the racemization reaction.

The racemization is conducted for a time sufficient to allow the desired racemization in the presence of the acid, preferably the hydrobromic acid, and at the temperature outlined hereinbefore.

The racemization can be conducted in any type of appropriate equipment. Since the process can be used as an adjunct to a process for preparing an L-isomer ester, the racemization can be conducted in equipment and under conditions which can allow subsequent reesterification of the enantiomorph acid. It has been found that racemization and reesterification cannot be accomplished simultaneously.

The process of the present invention allows for the easy racemization of bromoaliphatic acids such as 2-bromopropionic acid in the substantial absence of by-products. This factor facilitates the use of the resulting racemate in further resolution processes after reesterification. By "no by-product formation" is meant that at least 90% of the original bromoaliphatic acid is recovered after racemization as either the bromo or chloro derivative. Preferably, less than 10% and more preferably less than 1% chloroaliphatic acid is formed.

As used herein the term "in the substantial absence of ionized halogen other than bromine ion" is intended to mean that less than 5% of the ionized halogen in the solution being racemized is a halogen other than bromine.

The invention will be more fully illustrated in the examples which follow.

EXAMPLE 1

This example demonstrates that reduction in pH or a low native pH is required for racemization of D-2-bromopropionic acid. Seven samples containing 5 grams (4.2 milliliters) of D-2-bromopropionic acid, 2.3 grams (½ mole equivalent) $Na_2O_4$ and 28 milliliters water were treated for 1 hour at reflux under the conditions shown in TABLE III. The cooled product was anhydrous ether extracted and tested for optical rotation. Experiment 8 uses neat 2-bromopropionic acid having a native pH of about 2. The results are reported in TABLE II (Initial rotation was about +28).

TABLE I

| Experiment | Reaction Conditions |
| --- | --- |
| 1 | Adjust pH to 1 with 10% $H_2SO_4$ |
| 2 | Add 1.47 grams (0.015 mole) concentrated $H_2SO_4$ |
| 3 | Add 0.3 grams NaBr. Adjust pH to 1 with 10% $H_2SO_4$ |
| 4 | Add 0.3 grams NaBr and 1.47 grams (0.015 mole) concentrated $H_2SO_4$ |
| 5 | Add 1.5 grams NaBr. Adjust pH to 1 with 10% $H_2SO_4$ |
| 6 | Add 1.5 grams NaBr and 1.47 grams (0.015 mole) concentrated $H_2SO_4$ |
| 7 | Heat to reflux. Native pH 2.1 |
| 8 | Heat 2-bromopropionic acid to reflux. Native pH 2.1 |

TABLE II

| Experiment | Observed Optical Rotation (Neat) |
| --- | --- |
| 1 | −0.172° |
| 2 | −0.073° |
| 3 | −0.094° |
| 4 | −0.061° |
| 5 | −0.109° |
| 6 | −0.034° |
| 7 | −0.659° |
| 8 | −0.755° |

This data clearly shows racemization was accomplished at reduced pH.

EXAMPLE 2

This example demonstrates that the treatment of 2-bromopropionic acid in hydrochloric acid produces by-products.

Five grams (2.94 milliliters) of a raceme of 2-bromopropionic acid in 20 milliliters of water were treated for 1 hour under the conditions listed in TABLE I, the cooled product extracted with anhydrous ether and analyzed by gas chromatography. The results are reported in TABLE IV.

TABLE III

| Experiment | Reaction Conditions |
|---|---|
| 1 | Control - stir only at room temperature (about 20° C.) |
| 2 | Reflux - native pH 1.5 |
| 3 | Reflux - adjust pH to 1.0 with concentrated $H_2SO_4$ |
| 4 | Reflux - adjust pH to 1.0 with 6N HCl |
| 5 | Reflux - adjust pH to 1.0 |
| 6 | Reflux - adjust pH to less than 1 with 1N $H_2SO_4$ (0.7 milliliter concentration) |
| 7 | Reflux - adjust pH to less than 1N with 1N HCl (5 milliliters 6N HCl) |
| 8 | Reflux - adjust pH to less than 1 with 1N HBr (3.4 milliliters 47% HBr) |

TABLE IV

| Experiment | 2-Bromo Acid | 2-Chloro Acid | Other |
|---|---|---|---|
| 1 | 99 | — | — |
| 2 | 91 | — | 9 |
| 3 | 99 | — | — |
| 4 | 83 | 11 | 6 |
| 4 | 99 | — | — |
| 6 | 92 | — | 8 |
| 7 | 20 | 80 | — |
| 8 | 99 | — | — |

This example clearly shows that the presence of chlorine ion from hydrochloric acid will react with the raceme of 2-bromopropionic acid to form 2-chloropropionic acid (Experiments 4 and 7). The greater the quantity of chlorine ion, the greater the by-product formation.

The data also shows that when the pH is reduced below 1 with sulfuric acid (Experiment 6), other unidentified compounds appear in the gas chromatography analysis. This does not occur when using hydrobromic acid. Refluxing the raceme of 2-bromopropionic acid at native pH provided 9% unidentifiable by-product other than a 2-chloropropionic acid (Experiment 2).

What is claimed is:

1. A process for racemizing an optically active organic acid of the formula:

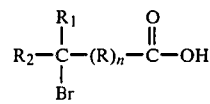

wherein R can be aliphatic or aromatic, $R_1$ and $R_2$ can each be hydrogen and alkyl of up to 20 carbon atoms wherein $R_1$ and $R_2$ are different and n is an integer of zero or 1 comprising heating an acidified solution of said optically active organic acid in the substantial absence of halide ion other than bromine ion in an amount sufficient and at a pH and temperature sufficient to racemize said optically active organic acid.

2. The process as recited in claim 1 wherein n is zero.

3. The process as recited in claim 1 wherein $R_1$ is hydrogen.

4. The process as recited in claim 1 which also includes the initial step of acidifying the solution with an acid other than hydrofluoric, hydrochloric or hydroiodic acid.

5. The process as recited in claim 4 wherein said acid is a mineral acid.

6. The process of claim 5 wherein said acid is hydrobromic acid.

7. The process as recited in claim 6 wherein said hydrobromic acid is used in an amount sufficient to provide a pH below about pH 2.5.

8. The process as recited in claim 6 wherein said organic acid is 2-bromopropionic acid.

9. The process as recited in claim 8 wherein said 2-bromopropionic acid is D-2-bromopropionic acid.

10. The process as recited in claim 1 wherein the bromine ion is provided by a source of bromine ion other than hydrobromic acid.

11. The process as recited in claim 1 wherein said heating is conducted at a temperature ranging from about 50° C. to reflux.

12. The process as recited in claim 11 wherein said heating is at reflux temperature.

13. The process as recited in claim 1 wherein said alkyl is $C_1$-$C_4$ alkyl.

14. The process as recited in claim 1 wherein said heating is conducted for a period of time sufficient to racemize the optically active organic acid to an enantiomeric excess of less than about 50%.

15. The process as recited in claim 1 wherein said heating is conducted for a period of time sufficient to racemize the optically active organic acid to an enantiomeric excess of less than about 30%.

16. The process as recited in claim 6 wherein n is zero.

17. The process as recited in claim 6 wherein $R_1$ is hydrogen.

* * * * *